(12) United States Patent  
Perez de Alderete et al.

(10) Patent No.: US 9,333,096 B2  
(45) Date of Patent: May 10, 2016

(54) PROSTHETIC LIMB

(71) Applicant: The University of Massachusetts, Boston, MA (US)

(72) Inventors: Jonathan Michael Perez de Alderete, Carlisle, MA (US); Erin Elizabeth Keaney, Groton, MA (US); Brendan Charles Donoghue, Shrewsbury, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 14/257,705

(22) Filed: Apr. 21, 2014

(65) Prior Publication Data

US 2015/0297363 A1    Oct. 22, 2015

(51) Int. Cl.
*A61F 2/56* (2006.01)
*A61F 2/58* (2006.01)
*A61F 2/54* (2006.01)
(Continued)

(52) U.S. Cl.
CPC ... *A61F 2/54* (2013.01); *A61F 2/60* (2013.01); *A61F 2/582* (2013.01); *A61F 2002/502* (2013.01); *A61F 2002/509* (2013.01); *A61F 2002/5018* (2013.01); *A61F 2002/5021* (2013.01); *A61F 2002/5024* (2013.01); *A61F 2002/5039* (2013.01); *A61F 2002/5083* (2013.01); *A61F 2002/5084* (2013.01); *A61F 2002/543* (2013.01); *A61F 2002/546* (2013.01); *A61F 2002/607* (2013.01); *A61F 2002/608* (2013.01)

(58) Field of Classification Search
CPC .................. A61F 2002/509; A61F 2002/5016; A61F 2002/5018; A61F 2002/502; A61F 2002/5021; A61F 2002/5024; A61F 2/54; A61F 2/60; A61F 2/582
See application file for complete search history.

(56) References Cited

U.S. PATENT DOCUMENTS 2,629,106 A * 2/1953 Snethun ........................ 623/63
3,400,408 A * 9/1968 Garcia ............................ 623/43
4,161,042 A   7/1979 Cottingham et al.
(Continued)

FOREIGN PATENT DOCUMENTS

CN    201085704 Y     7/2008
EP     1169982 A1 *   1/2002
(Continued)

OTHER PUBLICATIONS

Gelinas, Faber, Patterson, King; Univ. of Western Ontario, Canada; "The Effectiveness of Turnbuckle Splinting for Elbow Contractures," http://www.boneandjoint.org.uk/highwire/filestream/16939/field_highwire_article_pdf/0/74.full-text.pdf; Pub. Jun. 11, 1999.
(Continued)

*Primary Examiner* — Marcia Watkins
(74) *Attorney, Agent, or Firm* — Cantor Colburn LLP

(57) ABSTRACT

A prosthetic limb includes a plurality of extendable segments configured to adjust the length of the prosthetic limb. Also included is a first end assembly operatively coupled to the plurality of extendable segments, wherein the first end assembly is radially adjustable to manipulate the thickness of the prosthetic limb. Further included is a second end assembly operatively coupled to the plurality of extendable segments, wherein the second end assembly is radially adjustable to manipulate the thickness of the prosthetic limb.

17 Claims, 5 Drawing Sheets

(51) Int. Cl.
  *A61F 2/60*  (2006.01)
  *A61F 2/50*  (2006.01)

(56) References Cited

U.S. PATENT DOCUMENTS

| | | | |
|---|---|---|---|
| 4,650,492 | A | 3/1987 | Barkhordar et al. |
| 4,990,162 | A | 2/1991 | LeBlanc |
| 5,085,665 | A | 2/1992 | Radocy et al. |
| 5,100,403 | A * | 3/1992 | Hotchkiss et al. ............... 606/56 |
| 5,314,500 | A * | 5/1994 | Weddendorf ................... 623/57 |
| 5,466,261 | A | 11/1995 | Richelsoph |
| 5,993,487 | A | 11/1999 | Skardoutos et al. |
| 6,761,743 | B1 | 7/2004 | Johnson |
| 8,252,063 | B2 | 8/2012 | Stauch |
| 2004/0193266 | A1 | 9/2004 | Meyer |
| 2005/0234564 | A1 | 10/2005 | Fink et al. |
| 2008/0188952 | A1 * | 8/2008 | Veatch et al. ................... 623/57 |
| 2008/0269907 | A1 | 10/2008 | Puchhammer |
| 2013/0123940 | A1 | 5/2013 | Hurley et al. |
| 2014/0005798 | A1 | 1/2014 | Bache et al. |

FOREIGN PATENT DOCUMENTS

| | | |
|---|---|---|
| EP | 1611868 A2 | 1/2006 |
| EP | 1642550 A2 | 4/2006 |
| EP | 2500000 A1 | 9/2012 |
| WO | 2010018358 A2 | 2/2010 |

OTHER PUBLICATIONS

McCormick School of Engineering, McCormick Freshmen Design Prosthetic Fitting Solutions for Upper-Limb Amputees; www.mccormick.northwestern.edu/news/articles/2013/01/freshmen-design-prosthetic-fitting-for-upper-limb-amputees.html; Jan. 9, 2013.

* cited by examiner

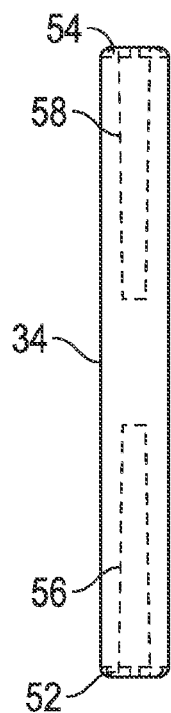
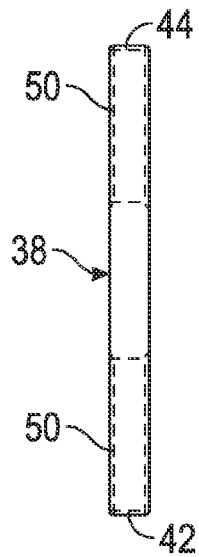
FIG. 4
FIG. 5
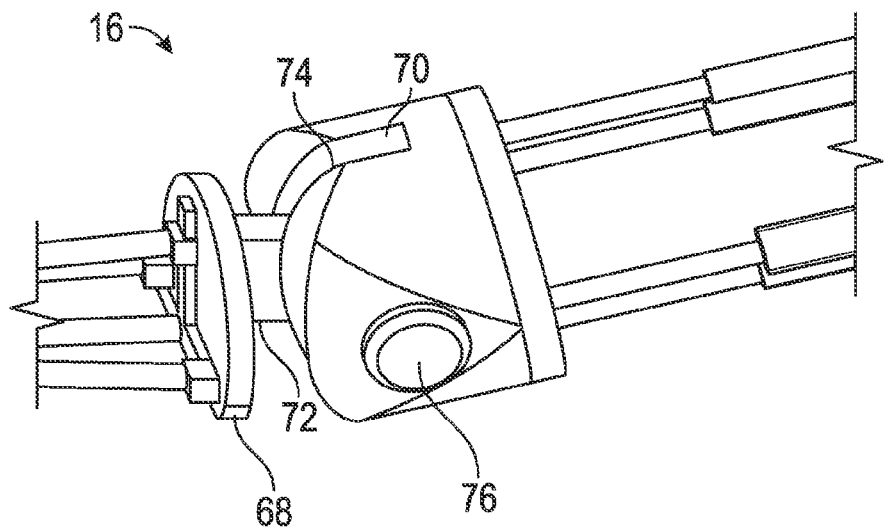
FIG. 6

PROSTHETIC LIMB

FIELD OF THE INVENTION

The subject matter disclosed herein relates to prosthetic limbs and, more particularly, to a prosthetic limb that is extendable to adjust to patient growth over time.

BACKGROUND OF THE INVENTION

Every year over a million cases of amputation due to injury, infection, and disease are reported. Traditionally, prosthetics have been designed as minimal functioning limbs in the form of hooks, sticks, and crutches, for example. The low cost associated with such examples is what drove the use of these types of items. In recent years, the complexity of prosthetics has increased to provide a user with enhanced functionality and aesthetic appeal. Consequently, the cost of prosthetics has increased drastically, thereby rendering state-of-the-art prosthetics unattainable for most users. Compounding this problem, pediatric patients require multiple prosthetic devices as the child grows.

BRIEF DESCRIPTION OF THE INVENTION

According to one aspect of the invention, a prosthetic limb includes a plurality of extendable segments configured to adjust the length of the prosthetic limb. Also included is a first end assembly operatively coupled to the plurality of extendable segments, wherein the first end assembly is radially adjustable to manipulate the thickness of the prosthetic limb. Further included is a second end assembly operatively coupled to the plurality of extendable segments, wherein the second end assembly is radially adjustable to manipulate the thickness of the prosthetic limb.

According to another aspect of the invention, a prosthetic limb includes a first limb portion assembly having a first plurality of extendable segments, a first end assembly, and a second end assembly. Also included is a second limb portion assembly having a second plurality of extendable segments, a third end assembly, and fourth end assembly. Further included is a joint assembly configured to join the first limb portion and the second limb portion. Yet further included is an appendage assembly operatively coupled to the first end assembly of the first limb portion, wherein the first plurality of extendable segments and the second plurality of extendable segments are extendable from an initial length to an extended length that is about two times the length of the initial length.

According to yet another aspect of the invention, a prosthetic lower limb includes a plurality of extendable segments configured to adjust the length of the prosthetic limb. Also included is a first end assembly operatively coupled to the plurality of extendable segments, wherein the first end assembly is radially adjustable to manipulate the thickness of the prosthetic limb. Further included is a second end assembly operatively coupled to the plurality of extendable segments, wherein the second end assembly is radially adjustable to manipulate the thickness of the prosthetic limb. Yet further included is an appendage assembly operatively coupled to the first end assembly, the appendage assembly comprising a foot assembly and an appendage attachment, wherein a first angle between the appendage attachment and the first end assembly is adjustable and a second angle between the appendage attachment and the foot assembly is adjustable, wherein adjustment of at least one of the first angle and the second angle adjusts a torque of each of the plurality of extendable segments to adjust a user gait.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

FIG. 4 is an elevational view of a turnbuckle of the sub-assembly illustrating interior threaded portions therein;

FIG. 5 is an elevational view of a rod of the sub-assembly illustrating exterior threaded portions thereon;

FIG. 6 is a perspective view of a joint assembly;

The detailed description explains embodiments of the invention, together with advantages and features, by way of example with reference to the drawings.

DETAILED DESCRIPTION OF THE INVENTION

Figure 1:
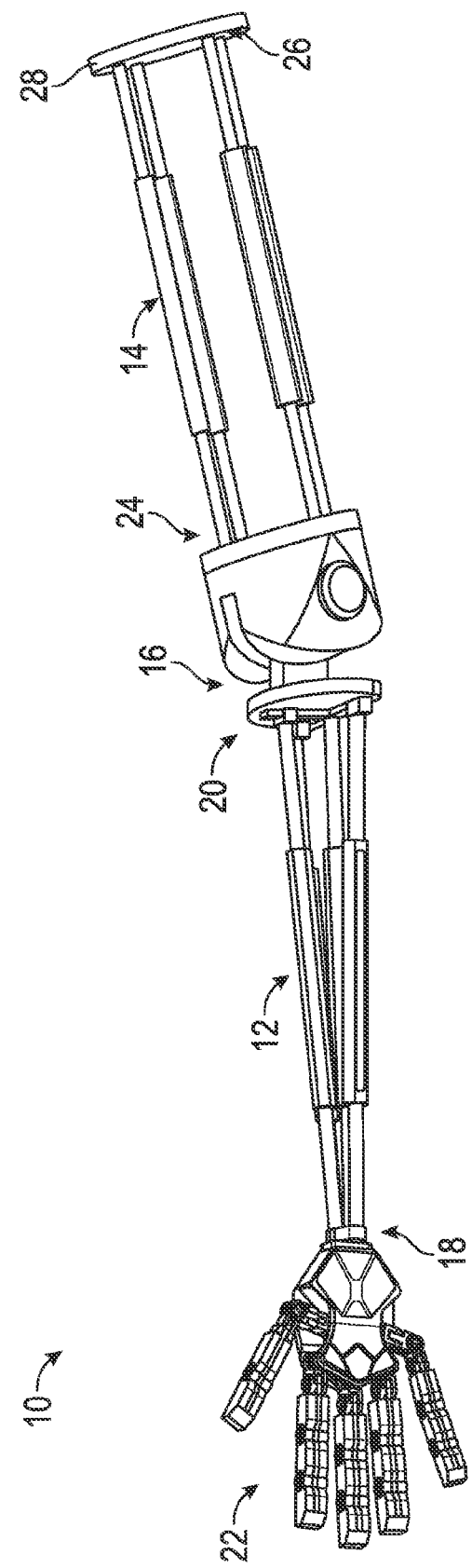
FIG. 1 is a perspective view of a prosthetic limb.

Referring to FIG. 1, an embodiment of a prosthetic limb is illustrated and generally referred to with numeral 10. The prosthetic limb 10 is formed of multiple sub-assemblies, including a first limb portion assembly 12 and a second limb portion assembly 14. In the illustrated embodiment, the prosthetic limb 10 comprises an upper body limb, namely an arm, with the first limb portion assembly 12 being disposed between the elbow and wrist (i.e., forearm, antebrachium) and the second limb portion assembly 14 being disposed between the elbow and shoulder (i.e., arm proper, brachium). Although illustrated and described herein as an upper body limb, it is to be appreciated that the prosthetic limb 10 may be slightly modified to function as a lower body limb. In such an embodiment, the first limb portion assembly 12 is disposed between a foot and a knee (i.e., leg) and the second limb portion assembly 14 is disposed between the knee and the hip (i.e., thigh), as shown in FIG. 10.

Irrespective of whether the prosthetic limb 10 is an upper or lower limb, the first limb portion assembly 12 is joined to the second limb portion assembly 14 with a joint assembly 16 that facilitates relative positional movement between the first limb portion assembly 12 and the second limb portion assembly 14. Additionally, the joint assembly 16 includes a locking mechanism that is configured to fix the relative position between the first limb portion assembly 12 and the second limb portion assembly 14. As shown, the first limb portion assembly 12 extends from a first end assembly 18 to a second end assembly 20. The first end assembly 18 is configured to be operatively coupled to an appendage assembly 22, such as the illustrated hand assembly or a foot assembly, while the second end assembly 20 is configured to be operatively coupled to the joint assembly 16. Similarly, the second limb portion assembly 14 is configured to be operatively coupled to the joint assembly 16 with a third end assembly 24, while a fourth end assembly 26 is configured to be operatively coupled to a cap 28 or the like, which functions as a terminal end of the prosthetic limb 10. The structural components of the prosthetic limb 10 are encased with a cover (not illustrated) that is formed of an elastomer or a similar suitable material (e.g., fabric) that is aesthetically appealing. Each of the aforementioned assemblies and components will be described in detail below.

Figure 2:
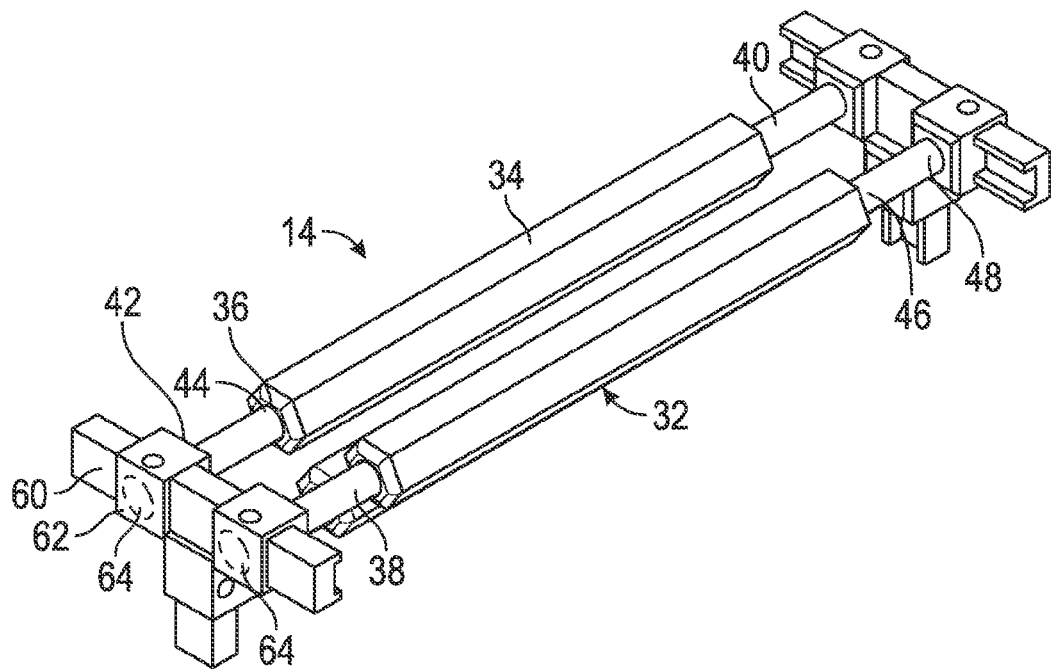
FIG. 2 is a perspective view of a sub-assembly of the prosthetic limb in a first configuration according to a first embodiment.
Figure 3:
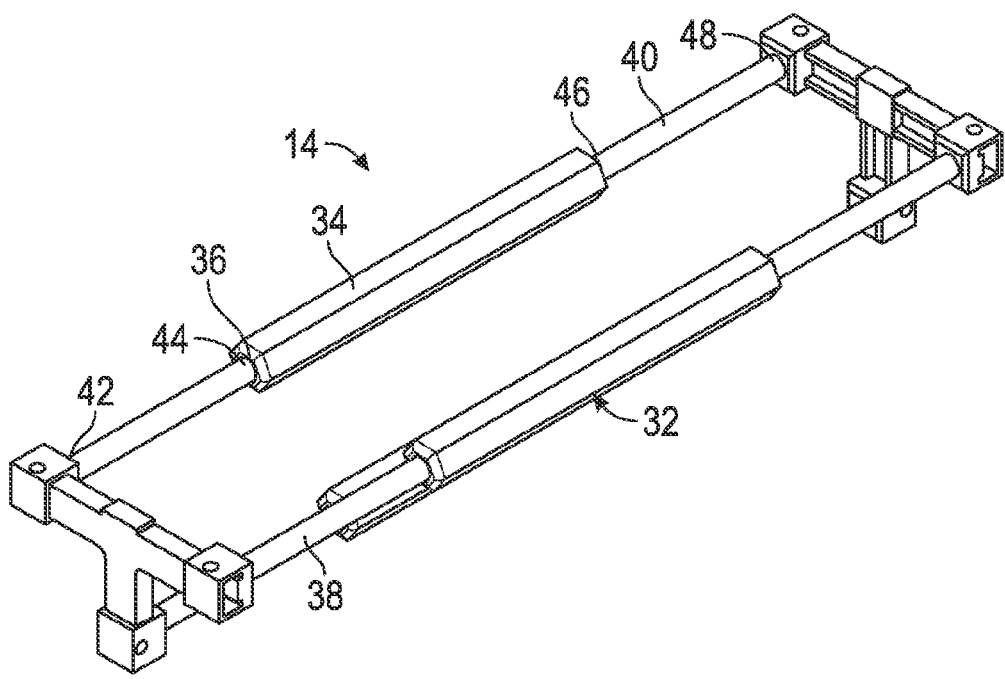
FIG. 3 is a perspective view of the sub-assembly of the prosthetic limb in a second, extended configuration according to the embodiment of FIG. 2.

Referring to FIGS. 2 and 3, the second limb portion assembly 14 is illustrated in greater detail and in two positional configurations. In particular, the second limb portion assembly 14 is moveable in both axial and radial directions to modify the overall dimensions of the prosthetic limb 10 from a first configuration (FIG. 2) to a second, larger configuration (FIG. 3). Extension of the second limb portion assembly 14 in the axial direction facilitates lengthening of the prosthetic limb 10, as needed, such as during the rapid growth of a child, for example. Radial manipulation of the second limb portion assembly 14 facilitates modification of the thickness of the prosthetic limb 10.

The second limb portion assembly 14 includes at least one, but typically a plurality of extendable segments 32 to extend and retract the limb. The plurality of extendable segments 32 each include a turnbuckle 34 having a hole 36 extending axially therethrough, with the hole 36 being defined by an interior surface of the turnbuckle 34. In the illustrated embodiment, the turnbuckle 34 has a polygonal outer surface, but as can be appreciated, numerous other outer surface geometries are contemplated. The plurality of extendable segments 32 also include a first rod 38 and a second rod 40 that are configured to be in threaded engagement with the turnbuckle 34. The first rod 38 includes a first end 42 and a second end 44, while the second rod 40 similarly includes a first end 46 and a second end 48. The first ends 42, 46 and the second ends 44, 48 of the first rod 38 and the second rod 40, respectively, each include threaded outer surfaces 50 (FIG. 5).

Referring to FIGS. 4 and 5, the turnbuckle 34 extends from a first end 52 to a second end 54. In one embodiment, the turnbuckle 34 is about 5.0 inches long. A first threaded region 56 of the turnbuckle 34 is located proximate the first end 52 within the hole 36 along the interior surface of the turnbuckle 34. Similarly, a second threaded region 58 is located proximate the second end 54 within the hole 36 along the interior surface of the turnbuckle 34. The threaded outer surface 50 of the second end 44 of the first rod 38 is sized and threaded to engage the first threaded region 56 of the turnbuckle 34, while the threaded outer surface 50 of the first end 42 of the second rod 40 is sized and threaded to engage the second threaded region 58 of the turnbuckle 34. In one embodiment, the first threaded region 56 and the second threaded region 58 are each about 2.0 inches in length. In one embodiment, the threaded outer surfaces 50 of the first rod 38 and the second rod 40 are each about 1.0 inch in length and the respective overall length of the first rod 38 and the second rod 40 is about 3.0 inches. In an embodiment, the outer diameter of the first rod 38 and the second rod 40, as well as the diameter of the hole 36 of the turnbuckle 34, is about 0.25 inches.

In operation, the threaded outer surfaces 50 of the first rod 38 and the second rod 40 are configured to engage the turnbuckle 34 and may adjusted to modify the length of the second limb portion assembly 14, thereby altering the length of the prosthetic limb 10. In contrast to traditional prosthetic limbs that only allow for fine-tuning of a limb length for customized fitting purposes, the length of the prosthetic limb 10 may be drastically altered, thereby allowing mass manufacturing of the prosthetic limb 10 to take advantage of economies of scale. In general, the limb portion assemblies 12, 14 may be extended to 200% of the contracted length. In one embodiment, the limb portion assemblies 12, 14 may be adjusted from the first configuration (FIG. 2) that has a length of about 6.0 inches to the second configuration (FIG. 3) that has a length of about 12.0 inches. However, it is to be appreciated that the particular dimensions may be scaled to facilitate effective usage by human children of all ages, human adults, and even animals of various sizes.

Referring again to FIGS. 2 and 3, the end assemblies of the first and second limb portion assemblies 12, 14 are axial end portions of the sub-assemblies. In the case of the second limb portion assembly 14, the third end assembly 24 and the fourth end assembly 26 are engaged with the first rod 38 and the second rod 40 of each of the plurality of extendable segments 32. In particular, the first end 42 of the first rod 38 is engaged with the third end assembly 24 and the second end 48 of the second rod 40 is engaged with the fourth end assembly 26. As described above, the first rod 38 and the second rod 40 each included threaded outer surfaces 50 proximate these regions and can be engaged with corresponding threaded regions of the third end assembly 24 and the fourth end assembly 26.

Each end assembly 24, 26 includes a plate member 60 and a plurality of slider members 62 that are slidably disposed on the plate member 60. The number of the plurality of slider members 62 corresponds to the number of the plurality of extendable segments 32, as each slider member is configured to engage and secure an end of the rods associated with each extendable segment. The plate member 60 may be formed of numerous contemplated geometries. In the illustrated embodiment, the plate member 60 comprises a substantially T-shaped geometry. The plurality of slider members 62 are configured to slide along each segment of the T-shaped geometry between radially inner and radially outer positions. Movement between these positions defines the radial position of the plurality of extendable segments 32, thereby defining the overall thickness of the prosthetic limb 10, as the cover moves inwardly or outwardly due to the fitted nature of the cover over these components. Engagement between the plurality of slider members 62 and the rods 38, 40 is made by threaded engagement between the threaded outer surfaces 50 of the rods 38, 40 and a threaded hole 64 located within each of the plurality of slider members 62. The radial position of each of the plurality of slider members 62 is locked into position with a compression socket and pin arrangement.

Figure 8:
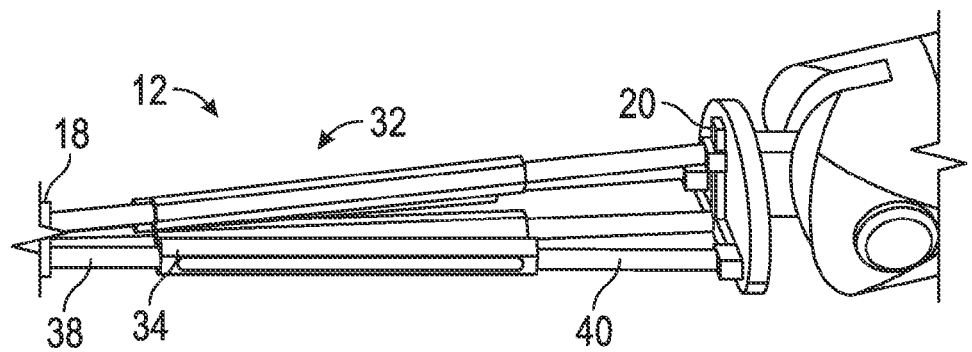
FIG. 8 is a perspective view of the sub-assembly according to another embodiment.

The first end assembly 18 and the second end assembly 20 are identical to that described above in conjunction with the third end assembly 24 and the fourth end assembly 26. In an alternative embodiment, the first end assembly 18 of the first limb portion assembly 12 that is operatively coupled to the appendage assembly 22 does not include the plurality of slider members 62. Rather, the first rod 38 of each of the plurality of extendable segments 32 are joined to the appendage assembly 22 at an angle in a fixed radial position, as shown in FIG. 8.

Figure 7:
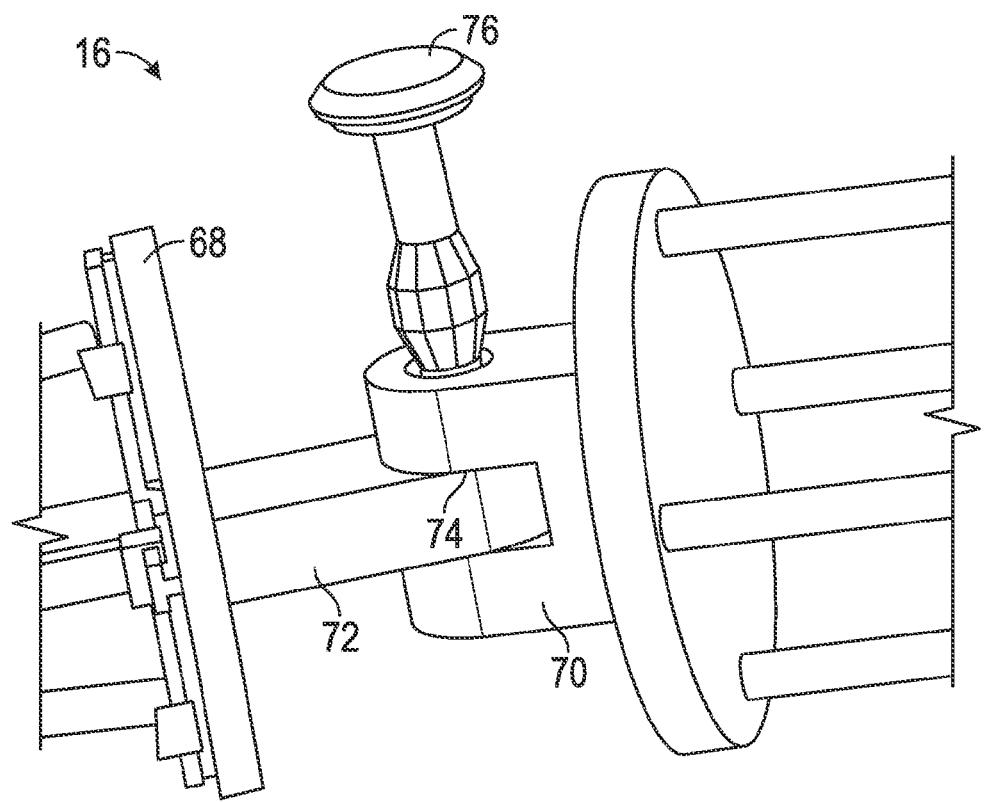
FIG. 7 is a perspective view of the interior of the joint assembly illustrating a positional locking mechanism.

Referring now to FIGS. 6 and 7, the joint assembly 16 is illustrated in greater detail. The joint assembly 16 comprises a gear arrangement that is actuated and locked manually. The joint assembly 16 includes a first member 68 and a second member 70 that are rotatable relative to each other. A pin portion 72 of the first member 68 is disposed within a socket portion 74 of the second member 70 to facilitate rotation. The rotational position of the first member 68 relative to the second member 70 is locked with a plunger 76 that is configured to mesh with the first member 68 and the second member 70. The plunger 76 includes a defined geometry that meshes with the members in an engaged position to lock the joint assembly 16 position. The plunger 76 may be pulled out (or forced out from the other side) to disengage the plunger 76 and allow for repositioning of the joint assembly 16.

Figure 9:
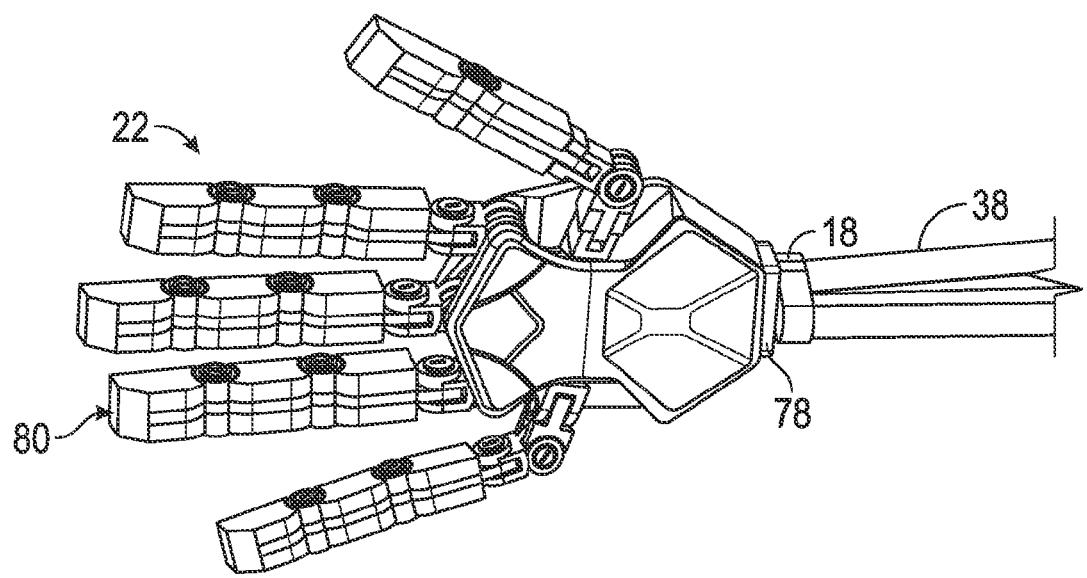
FIG. 9 is a perspective view of a hand assembly.

Referring now to FIG. 9, the appendage assembly 22 is illustrated in greater detail. As described in detail above, the first end assembly 18 of the first limb portion assembly 12 is operatively coupled to the appendage assembly 22. In the case of an upper body limb, the appendage assembly 22 comprises a hand assembly, as shown in the illustrated embodiment. As noted above, a foot assembly may be operatively coupled thereto for a lower body limb, as shown in FIG. 10.

In one embodiment, the first end assembly 18 is operatively coupled to the appendage assembly 22 with an appendage attachment 78. The appendage attachment 78 may be compatible with current prosthetic hands and features natural angles to ensure the limb is properly shaped. For lower limbs (FIG. 10), the plane (e.g., relative angle between the appendage attachment 78 and the first end assembly 18 or the foot appendage) can be adjusted to correct gait by increasing or decreasing the torque on the part in the plurality of extendable segments 32. The purpose of this adjustment is to allow for correction of gait for lower limb amputees, as well as for proper angling for upper body amputees. The angular adjustment can be as extreme as 20 degrees from the normal. This planar adjustment is further facilitated through plastic components. The appendage attachment 78 is configured to rotate a full 360 degrees to allow convenient repositioning of the appendage assembly 22, such as the hand.

In the case of a hand assembly, the appendage assembly 22 features individual fingers 80 that include an opposable thumb and pinky. A control system is provided and may be adapted based on the need of the patient without changing the base model. The control system may be body powered, cable driven, or motorized. The fingers 80 are detachable and re-attachable and may be relocated to adjust the hand assembly from a left hand to a right hand, or vice versa. This is yet another example of a customizable modification available to a broad patient base, thereby facilitating mass manufacturing and lower cost for consumers. It is to be appreciated that although the appendage assembly 22 is illustrated and described herein as being employed with the particular prosthetic limb 10 described herein, the appendage assembly 22 may be attached to preexisting prosthetic arms and can be broken down into digits to form a partial hand prosthetic.

Most or all of the above-described components are injection molded components that are formed of one or a combination of plastic materials. Exemplary, but not limiting, materials used to form the components include high impact polystyrene (HIPS), polycarbonate, nylon, and polyether ether ketone (PEEK). The advantage of plastic is the weight. The weight of a lower limb can be reduced to a tenth of the weight of a lower limb that is formed mainly of wood or metal components. Reduced weight increases patient comfort and wear time. Additionally, the limb may be worn in water and in hostile terrain without major detriments.

Advantageously, the prosthetic limb 10 is configured to "grow" with the child, in the case of a pediatric patient. Additionally, the components of the prosthetic limb 10 are injection molded and formed of low cost plastic materials, thereby reducing cost and allowing for mass production of limbs. This allows production of a basic model and allows a user to customize the configuration and dimensions of the prosthetic limb 10, rather than requiring individual manufacture and customization for each patient.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A prosthetic limb comprising:
a plurality of extendable segments configured to adjust a length of the prosthetic limb;
a first end assembly operatively coupled to the plurality of extendable segments, wherein the first end assembly is radially adjustable to manipulate a first end thickness of the prosthetic limb; and
a second end assembly operatively coupled to the plurality of extendable segments, wherein the second end assembly is radially adjustable to manipulate a second end thickness, the first end thickness and the second end thickness each adjusting an overall thickness of the prosthetic limb, wherein each of the first end assembly and the second end assembly comprises:
a plate member; and
a plurality of slider members operatively connected to the plate member, wherein a number of the plurality of slider members of each of the first end assembly and the second end assembly are lockable and corresponds to a number of the plurality of extendable segments, each of the first end assembly plate member and the second end assembly plate member comprising a T-shaped geometry and the number of the plurality of slider members of each of the first end assembly and the second end assembly is at least three.

2. The prosthetic limb of claim 1, wherein each of the plurality of extendable segments comprises:
a first rod having a first end and a second end;
a second rod having a first end and a second end; and
a turnbuckle having a first end, a second end, a hole defined by an internal surface and extending axially therethrough from the first end to the second end of the turnbuckle, a first threaded region along the internal surface and proximate the first end of the turnbuckle, and a second threaded region along the internal surface and proximate the second end of the turnbuckle.

3. The prosthetic limb of claim 2, wherein the second end of the first rod is in threaded engagement with the first threaded region of the turnbuckle and the first end of the second rod is in threaded engagement with the second threaded region of the turnbuckle.

4. The prosthetic limb of claim 2, wherein the first end of the first rod is operatively coupled to the first end assembly and the second end of the second rod is operatively coupled to the second end assembly.

5. The prosthetic limb of claim 2, wherein the turnbuckle comprises a turnbuckle length of at least 4.0 inches and the first threaded region and the second threaded region of the turnbuckle are each at least 2.0 inches in length.

6. The prosthetic limb of claim 2, wherein the first rod, the second rod, and the hole of the turnbuckle each have a diameter of at least 0.25 inches.

7. The prosthetic limb of claim 1, wherein the first end assembly, the second end assembly, and the plurality of extendable segments are formed of at least one plastic material and are injection molded components.

8. The prosthetic limb of claim 1, wherein the plate member of each of the first end assembly and the second end assembly and the plurality of slider members of each of the first end assembly and the second end assembly are formed of at least one plastic material and are injection molded components.

9. The prosthetic limb of claim 1, wherein each of the plurality of slider members of each of the first end assembly and the second end assembly is locked into position with compression of a pin arrangement.

10. The prosthetic limb of claim 1, wherein the first end assembly is operatively coupled to an appendage assembly.

11. The prosthetic limb of claim 10, wherein the appendage assembly comprises an appendage attachment and a hand assembly.

12. The prosthetic limb of claim 11, wherein the hand assembly comprises reconfigurable fingers that includes an opposable thumb.

13. The prosthetic limb of claim 11, wherein the hand assembly is rotatable about a 360 degree angle relative to the appendage attachment, wherein a first angle between the appendage attachment and the first end assembly is adjustable and a second angle between the appendage attachment and the appendage assembly is adjustable, wherein adjustment of at least one of the first angle and the second angle adjusts a torque of each of the plurality of extendable segments.

14. The prosthetic limb of claim 1, wherein the second end assembly is operatively coupled to a joint assembly comprising a first member and a second member rotatable relative to each other and positionally lockable with a plunger configured to extend through apertures of the first member and the second member.

15. The prosthetic limb of claim 1, wherein the plurality of extendable portions are configured to extend from an initial length to 200% of the initial length.

16. A prosthetic limb comprising:

a first limb portion assembly having a first plurality of extendable segments, a first end assembly, and a second end assembly;

a second limb portion assembly having a second plurality of extendable segments, a third end assembly, and fourth end assembly;

a joint assembly configured to join the first limb portion assembly and the second limb portion assembly; and an appendage assembly operatively coupled to the first end assembly of the first limb portion, wherein the first plurality of extendable segments and the second plurality of extendable segments are extendable from an initial length to an extended length that is less than about three times the initial length, wherein each of the end assemblies comprises:

a plate member; and a plurality of slider members operatively connected to the plate member, wherein a number of the plurality of slider members of each of the end assemblies are lockable and corresponds to a number of the plurality of extendable segments, each of the first end assembly plate member, the second end assembly plate member, the third end assembly plate member and the fourth end assembly plate member comprising a T-shaped geometry and the number of the plurality of slider members of each of the end assemblies is at least three.

17. The prosthetic limb of claim 16, wherein the appendage comprises at least one appendage assembly operatively coupled to the first end assembly with an appendage attachment.

* * * * *